United States Patent [19]

Durand et al.

[11] 4,119,494

[45] Oct. 10, 1978

[54] IMMOBILIZATION OF ENZYMES IN AN ANHYDROUS MEDIUM

[75] Inventors: Gilbert Durand; Pierre Monsan, both of Toulouse, France

[73] Assignee: Rhone-Poulenc Industries, Paris, France

[21] Appl. No.: 752,135

[22] Filed: Dec. 20, 1976

Related U.S. Application Data

[63] Continuation-in-part of Ser. No. 494,818, Aug. 5, 1974, abandoned.

[51] Int. Cl.² ................................................. C07G 7/02
[52] U.S. Cl. ............................... 195/68; 195/DIG. 11
[58] Field of Search ..................... 195/63, 68, DIG. 11

[56] References Cited

U.S. PATENT DOCUMENTS

| 3,691,016 | 9/1972 | Patel ........................................ 195/68 |
| 3,766,013 | 10/1973 | Forgione et al. .................. 195/68 X |
| 3,847,743 | 11/1974 | Forgione et al. .................. 195/68 X |

OTHER PUBLICATIONS

Monsan et al., Nouvelle Methode de Preparation d'Enzymes Fixes sur des Supports Mineraux, C. R. Acad. Sci. Paris, T. 273, Jul. 5, 1971 (pp. 33–36).
Bartling et al., Synthesis of a Matrix-Supported Enzyme in Non-Aqueous Conditions, Nature, vol. 243, Jun. 1973, (pp. 342–344).

*Primary Examiner*—David M. Naff
*Attorney, Agent, or Firm*—McDougall, Hersh & Scott

[57] ABSTRACT

Fixing of enzymes to a mineral, organic or organomineral support is carried out in an anhydrous organic liquid medium at a temperature above 60° C up to 120° C. Fixation in an anhydrous liquid medium permits obtaining support - enzyme complexes with a fast fixation reaction speed at high temperatures and without any particular pH value condition.

9 Claims, No Drawings

IMMOBILIZATION OF ENZYMES IN AN ANHYDROUS MEDIUM

This application is a continuation-in-part of our co-pending application Ser. No. 494,818, filed Aug. 5, 1974, now abandoned, and entitled Process For Fixing Enzymes On Supports.

The present invention relates to a process for fixing enzymes upon supports in an organic medium. It also relates to the support-enzyme complexes obtained by the said process.

It is known that the use of enzymes for industrial purposes is limited by the instability of the enzyme, the frequently large quantities required to be utilized, and consequently the high cost.

In order to have more rational utilization of enzymes it was proposed to immobilize them on supports by adsorption, inclusion in insoluble gels, reticulation, or covalent bond between the support and the enzyme. The latter technique, which is used most frequently by reason of the properties of the enzymatic derivatives obtained, is generally carried out by placing the water-soluble or insoluble support in contact with the enzyme in a totally or partially aqueous medium maintained at a pH level where the enzyme is stable and active, at a temperature below 50° C.

However, the speed of the fixation reaction is slow, adsorption phenomena occur in the course of the reaction, the support-enzyme complexes obtained still lack stability and their activity is weak. Moreover, in the course of the fixation reaction, there is competition frequently between the enzyme molecules and the water molecules to substitute the reactive groups of the support, which limits the quantity of active enzyme which is fixed.

The object of this invention is to diminish these drawbacks and permit the obtaining, with a fast fixation reaction speed and without any particular pH value condition, support-enzyme complexes in which the quantity of fixed active enzyme is high, which resist denaturation factors: preservation, temperature, pH value, and are more active than the known complexes.

The process, according to the invention, consists in realizing the fixation of enzymes on supports and is characterized in that the fixing is effected in anhydrous organic medium at a temperature within the range of more than 60° C. up to 120° C.

The enzymes which can be fixed, according to the process of the invention, are represented by:

The oxydoreductases, such as glucose oxidase, glutamic dehydrogenase, malic dehydrogenase, lactic dehydrogenase, peroxydase, and catalase;

the transferases, such as aspartate aminotransferase, histamine methyl fransferase, glycine amino transferase, aspartate acetyl transferase, E-lysine acetyl transferase, hexokinase, and fructokinase;

the hydrolases, such as lipase, phospholipase, acetyl cholinesterase, pectinase, phosphatase, $\alpha$ and $\beta$ amylase, maltase, cellulase, invertase, acylase, pepsin, papain, rennin, trypsin, chymotrypsin, asparaginase, urease, arginase, and ribonuclease, glucoamylase;

lyases, such as aspartate decarboxylase, glutamate decarboxylase, malate synthase, citrate lyase, and fumaratehydratase;

isomerases, such as alanine racemase, methionine racemase, glutamate racemase, lactate racemase, and glucose phosphate isomerase;

ligases, such as asparagine synthetase, glutamine synthetase, glutathion synthetase, and pyruvate synthetase.

The mineral, organic or organo-mineral support utilized is insoluble in the organic medium and must be active, that is to say, possess one or more functional groups reactive with groups such as amine, carboxyl, sulphydryl, hydroxyl, by which the enzymes can be fixed. When the support does not in itself possess the said functional groups, it must be modified.

As support mention can be made of: brick, silica, alumina, the clays, sand, agarose, starch, polydextrane, cellulose, polymers such as polybutadiene, polystyrene whether or not cross-linked, copolymers of methacrylic acid and copolymers of maleic anhydride and ethylene.

The modification or activation of the support consists in treating the said support so as to supply it with the functional group or groups reacting with the enzyme. This modification is effected according to well-known processes and is a function of the nature of the support utilized and of the nature of the enzyme to be fixed. Among these activations, making use of conventional chemical reactions, such as diazotization, halogenation, sulphonation, one may mention the reactions of the support with for example a halide of sulphuryl, cyanuryl, cyanogen, thionyl, the grafting of the support, especially the polymers by hydrolyzable polyfunctional silanes of carbonyl groups.

These supports are generally employed in the form of grains, the granulometry of which, in most cases greater than 100$\mu$ can be greatly varied. They must be free from all products which inhibit or denature the enzyme and free from all traces of water.

The organic medium, in which the enzyme is insoluble, is selected from among the aliphatic, cycloaliphatic or aromatic hydrocarbons, possibly containing chlorine atoms or hetero atoms, such as atoms of oxygen and/or sulphur. They are represented by: hexane, benzene, toluene, xylene, chloroform, carbon tetrachloride; dichloroethane, trichloroethane, trichloroethylene, perchloroethylene, dioxane, tetrahydrofuran, and dimethylsulphoxide. These hydrocarbons are used along or in mixtures.

According to the process of the invention, the active support and one or more enzymes are dispersed simultaneously or successively in the hydrocarbon, then the reaction medium is brought to the reaction temperature, preferably the boiling temperature of the medium, for the time necessary for the fixing of the enzyme.

The desired fixation at a rapid rate without excessive loss if any of enzymatic activity can be achieved in accordance with the practive of the invention at reaction temperature within the range of above 60° C. up to 120° C. It is believed that the ability to make use of such high temperature for rapid fixation of the enzymes on the solid particulate support depends upon the reaction being carried out in the non-aqueous organic liquid medium since the reaction at such temperature levels in aqueous medium would denature the enzyme and destroy its enzymatic activity.

The amount of enzyme used is in excess in relation to the functional groups of the support. As regards the hydrocarbon, the quantity utilized, which is variable with the nature of the support and the nature of the enzyme, must be sufficient to obtain a good dispersion which permits contact between the active support and the enzyme.

It is very surprising that such high temperatures permit the fixing of the enzymes without the enzymatic activity being considerably reduced, since it was heretofore accepted that temperatures higher than 40°–50° C. denatured the enzymes.

In order to accelerate the reaction it is possible to operate under a slight pressure.

Contrary to the known processes, the pH value of the fixation medium has no influence upon the properties of the enzyme fixed.

The reaction time is generally between several minutes and 2 hours, which represents a considerable gain in time in comparison with the known processes.

After fixing, the hydrocarbon is easily separated and the support-enzyme complex obtained is washed with the aid of a buffer solution which is variable with the enzyme, and such that its pH value and its composition have no denaturing action upon the complex. This washing permits separation of the enzyme which has not reacted and that which is simply adsorbed upon the support. This separated enzyme is recovered and can be re-utilized in another fixation reaction.

The obtained support-enzyme complexes are constituted by one or more enzymes fixed on the support. In the case where the complex contains several enzymes, these are fixed either simultaneously or successively, according to the invention, or the complex is obtained by mixing of two complexes prepared in accordance with the invention.

The quantities of enzyme fixed by covalent bonding, according to the process of the invention, are a function of the nature of the enzyme and of the nature and structure of the support and are clearly greater than the quantities of enzyme fixed according to the process in aqueous medium.

The support-enzyme complexes of the invention can be utilized at higher temperatures than the complexes prepared in aqueous medium. Moreover they are advantageously usable continuously for relatively long times without loss of activity or with a slight loss of activity of the enzyme.

The support-enzyme complexes can be used as catalyst of high specific or controlled activity, in medicine, pharmacy, chemical and foodstuffs industries, and tanning.

Some examples of realization of the invention are given hereinafter by way of illustration and not of limitation.

EXAMPLE 1

Fixing of pectinase on brick

Brick, which is crushed and screened so as to have a homogeneous granulometry, that is a diameter between 0.5 and 0.8 mm, is washed with distilled water and then with an aqueous solution of N hydrochloric acid and finally with distilled water. After 15 hours at 700° C. in an oxygen atmosphere, the impurity-free brick is activated: 2 g of brick are introduced into 40 ml of a 10% solution by volume of sulphuryl chloride in anhydrous benzene (B.P. 80° C.). The obtained suspension is agitated and brought to the boiling temperature of the mixture, which temperature is maintained for 20 hours. The active brick formed is then separated.

0.5 g of commercial pectinase, then 2 g of active brick are dispersed by sonic vibration in 50 ml of anhydrous benzene. The obtained dispersion is heated to the boiling temperature and kept at this temperature for 1 hour.

After cooling, the solid is filtered under vacuum, washed by placing in contact for 15 hours at 4° C. with 20 ml of a solution of M sodium chloride, centrifuged and dried. This washing operation is carried out seven times. It permits desorbing the enzyme adsorbed on the support, which can be re-utilized.

After each washing of the solid constituted by the support-enzyme complex, in which the enzyme is fixed on the support by covalent bonding, the enzymatic activity is determined as follows 1 g of the complex is dispersed in 10 ml of a 0.4% by weight solution of polygalacturonic acid in 0.01 M acetate buffer at pH 4. The dispersion is heated to 35° for 30 minutes. After cooling and decanting, 5 ml of the solution are extracted, then clarified by addition of 0.3 ml of a 9% by weight solution of zinc sulphate in water and 0.3 ml of an N aqueous solution of soda. After centrifuging, the reducing compounds present in the surface-floating portion are determined by the dinitrosalicylate method.

By way of comparison, the same test is repeated but the fixing is effected in aqueous medium with a solution of 0.5 mg of pectinase in 50 ml of water, 2 g of active brick, at 4° C. for 7 hours.

The results obtained are summarized in Table I where they are expressed in percentages of activity of the complex in comparison with the activity of the enzyme before fixing.

Table I

| Number of washings with M NaCl | | 1 | 2 | 3 | 4 | 5 | 6 | 7 |
|---|---|---|---|---|---|---|---|---|
| Activity | fixing in benzene medium | 69 | 50 | 47 | 47 | 47 | 47 | 47 |
| | fixing in aqueous medium | 44.5 | 39 | 36 | 32 | 28 | 27.5 | 24 |

By comparison it is observed that the fixing of the enzyme in benzene medium is more rapid than in aqueous medium.

Examination of the table shows that pectinase fixed in organic medium is more stable than that fixed in aqueous medium. Moreover, one notes a slight reduction of the activity, then a constant activity after the third washing for pectinase fixed in organic medium, whereas the activity of pectinase fixed in aqueous medium diminishes continuously. From this, it is deduced that the quantity of enzyme fixed by covalence in organic medium is clearly greater than that fixed in aqueous medium.

EXAMPLE 2

Fixing of papain on brick 2 mg of papain, 2 g of active brick, identical with that of Example 1, are placed in suspension in 20 ml of hexane (B.P. 69° C.). The suspension obtained is then heated under reflux for one hour.

After cooling, the solid is separated, washed with water, wash ed with 20 ml of an M sodium chloride solution, then again with water.

The enzymatic activity is measured on the support-enzyme complex obtained: The support-enzyme complex is placed in suspension in 1 ml of water; 9 ml of a solution of casein of 0.3% by weight in 0.025 M phosphate-citrate buffer, pH 7, are added and the suspension is heated to 37° C. for 10 minutes. After cooling and decanting, 4 ml of the solution are taken and 4 ml of a 10% by weight aqueous solution of trichloroacetic acid are added, the excess casein is precipitated, it is filtered, then the peptide content is determined on the filtrate, by Lowry's method.

The support-emzyme complex is washed again with water, with M NaCl and with water and a fresh measurement of the enzymatic activity is effected. These operations are repeated several times.

By way of comparison the fixing of papain on the same support is effected in aqueous medium at 4° C. for 7 hours. After washing, the enzymatic activity is measured as above.

The results, expressed in μg. of peptides liberated per ml and per minute are entered in Table II.

Table II

| Number of washings | | 5 | 10 | 15 |
|---|---|---|---|---|
| Activity | fixing in hexane | 3.2 | 1.6 | 1 |
| | fixing in water | 0.3 | 0.2 | 0.1 |

By comparison it is observed that the fixing time of the papain in hexane is shorter and that the quantity of enzyme fixed is 10 times higher than when one operates in water.

EXAMPLE 3

Fixing of trypsin on brick

Example 2 is repeated, the papain being replaced by trypsin.

The results obtained are entered in Table III.

Table III

| Number of washings | | 5 | 10 | 15 |
|---|---|---|---|---|
| Activity | fixing in hexane | 4.8 | 2.6 | 1.4 |
| | fixing in water | 0.6 | 0.3 | 0.1 |

This example shows that the time of fixing of trypsin in hexane is shorter than in water and that moreover the quantity of enzyme fixed is higher and that it is more stable.

The support-enzyme complex prepared in hexane is relatively stable, despite the successive washings which deteriorate the complex. This stability is greater if the complex is used continuously. Thus 50 g of active brick-trypsin complex, prepared as above, are placed in a column, where they are kept at 37° C. A solution of casein of 0.3% by weight in 0.025 M phosphate-citrate buffer pH 7, passes continuously through the column for 15 days at the rate of 60 ml/h.

Measurements of activity are determined as above every 24 hours. After 15 days the activity has diminished only by 5%.

This clearly shows the stability of the complexes according to the invention.

EXAMPLE 4

Fixing of ribonuclease on polybutadiene

Polybutadiene is activated by reaction with acetyl chloride.

20 mg of enzyme are placed in suspension in 50 ml of benzene, 2 g of active polybutadiene are added, then the obtained suspension is heated to boiling and kept at this temperature for 1 hour.

The fixing of the enzyme can be followed by infra-red spectroscopy. The absorption band at 1720 cm$^{-1}$ from the carbonyl group, which the active polybutadiene possesses, disappears in the course of fixing, while at 1640 cm$^{-1}$ an absorption band appears which is attributable to the imine function.

After separation, the support-enzyme complex formed is washed with 20 ml of carbonate buffer at pH 10.5, in order to eliminate the adsorbed enzyme. The activity of the fixed enzyme is then measured in relation to a purified ARN preparation.

20 mg of the obtained support-enzyme complex are placed in suspension in a mixture of 1 ml of 0.2 TRIS buffer, pH 7.8, containing 0.02 M EDTA, 1 ml of water and 1 ml of ARN in solution in water at a concentration such that there are 3.3 mg of ARN per ml of mixture.

The suspension is maintained for 2 minutes at 37° C., then 1 ml of Fayden's reagent is added thereto, it is left to rest for 15 minutes at 0° C., then centrifuged for 5 minutes at 6,000 rpm at 3° C., to separate the excess ARN. The separated supernatent solution is diluted to 1/30th and its absorption is measured at 260 nm, in comparison with a support without enzyme.

The enzymatic activity corresponds to 1.2 mg of active enzyme per g of support.

EXAMPLE 5

Fixing of glucoamylase on silica

A silica of 15 sq. m./g surface area is activated by grafting of a silane with epoxy function.

1 g of active support is added to 50 ml of a dispersion of chloroform (B.P. 61° C.) containing 20 mg of glucoamylase. The obtained suspension is heated under reflux for 2 hours.

After cooling, the complex formed is decanted, dried and rinsed three times with 20 ml of distilled water, and then it is washed for 24 hours at 4° C. with 20 ml of 2M NaCl.

By way of comparison, the same test is carried out in aqueous medium with 50 ml of a 0.1 M acetate buffer solution, pH 4.5, containing 20 mg of glucoamylase and 1 g of the same support, which is left in contact for 66 hours at 4° C. under agitation. After decanting, rinsing, and washing as above, the activity is measured.

The obtained support-enzyme complexes are introduced into 10 ml of a solution of starch at 3% by weight in a 0.1 M acetate buffer, pH 4.5, and left in contact with agitation for 10 minutes at 40° C. After separation, a determination of the reducing sugars is effected on the liquid phase, by colorimetry with 3.5-dinitrosalicylic acid. Several washings and measurements of activity are thus effected in succession. The results expressed in optical density are summarized in Table IV.

Table IV

| Fixing medium | Activity | |
|---|---|---|
| | 1 washing with 2 M NaCl | 7 days and 3 washings with 2 M NaCl |
| Chloroform | 0.800 | 0.564 |
| Water | 0.180 | 0.120 |

As in the previous examples, the fixing time of the glucoamylase in chloroform is shorter than in water and the complexes obtained are more active and more stable.

EXAMPLE 6

Fixing of invertase on brick 0.2 g of invertase, 2 g of active brick, identical with that of Example 1, are placed in suspension in 20 ml of toluene. The suspension obtained is then heated under reflux (about 111° C.) for 1 hour.

After cooling, the solid is separated, washed with water, washed with 20 ml of an M sodium chloride solution, then again with water.

The enzymatic acitivity is measured on the support-enzyme complex obtained. 500 mg of the complex is placed in suspension in 5 ml of distilled water; 10 ml of an 0.0585 M saccharose solution in distilled water and 5 ml of 0.2 M acetate buffer, pH 5.2 are added and left in contact for 30 mn at 40° C.

The reaction is stopped by decanting. The liquid phase is heated under reflux for 5 mn, then the reducing sugars are determined by the dinitrosalicylate method.

The support-enzyme complex is washed again with water, with M NaCl and with water and a fresh measurement of the enzymatic activity is effected as above. These operations are repeated several times.

By way of comparison, the fixing of invertase on the same support is effected in aqueous medium at 4° C. for 7 hours. After washing, the enzymatic activity is measured as above.

The results, expressed in mg of reducing sugars liberated by 1 are summarized in the table.

| Number of washings | | 1 | 2 | 3 |
|---|---|---|---|---|
| Activity | fixing in toluene | 85 | 80 | 78 |
| | fixing in water | 22 | 15 | 9 |

By comparison it is observed
(a) that the enzyme fixed at 111° C. is not denatured;
(b) that the quantity of enzyme fixed is 4 times higher when one operates in toluene at 111° C. for 1 hour than when one operates in water at 4° C. for 7 hours;
(c) that the enzyme fixed in toluene is more stable than that fixed in water.

We claim:
1. Process for fixing enzymes on supports comprising providing a solid support having groups which react with the enzymes to fix the enzyme to the support, reacting the enzyme with the support at a temperature within the range of more than 60° C. up to 120° C. in an anhydrous organic liquid in which both the enzyme and support are insoluble.

2. Process as claimed in claim 1 in which the enzymes to be fixed are selected from the group consisting of oxydoreductases, transferases, hydrolases, lyases, isomerases, and ligases.

3. Process as claimed in claim 1 in which the support is a material selected from the group consisting of a mineral, organic or organomineral material.

4. Process as claimed in claim 3 in which the support is selected from the group consisting of brick, silica, alumina, clay, sand; a natural organic polymer selected from the group consisting of agarose, starch, polydextran, cellulose; or a synthetic organic polymer selected from the group consisting of polybutadiene, polystyrene, copolymers of methacrylic acid and copolymers of maleic anhydride-ethylene.

5. Process as claimed in claim 1 in which the support is an activated support.

6. Process as claimed in claim 1 in which the organic liquid medium is selected from the group consisting of unsubstituted and chlorosubstituted aliphatic, cycloaliphatic and aromatic hydrocarbons, with or without oxygen and/or sulphur atoms.

7. Process as claimed in claim 1 in which the reaction is carried out under slight pressure.

8. Process as claimed in claim 1 in which the reaction for fixing the enzyme onto the support is carried out for a time within the range of several minutes to 2 hours.

9. Process as claimed in claim 1 in which the organic liquid medium is selected from the group consisting of hexane, benzene, toluene, xylene, chloroform, carbontetrachloride, dichloroethane, trichloroethane, trichloroethylene, perchloroethylene, dioxane, tetrahydrofuran, and dimethylsulphoxide.

* * * * *

UNITED STATES PATENT AND TRADEMARK OFFICE
CERTIFICATE OF CORRECTION

PATENT NO. : 4,119,494
DATED : October 10, 1978
INVENTOR(S) : Gilbert Durand et al.

It is certified that error appears in the above—identified patent and that said Letters Patent is hereby corrected as shown below:

On the cover sheet insert Priority Data:

--August 22, 1973      France      73.30413

Signed and Sealed this

First Day of April 1980

[SEAL]

Attest:

SIDNEY A. DIAMOND

Attesting Officer      Commissioner of Patents and Trademarks